United States Patent
Hong et al.

(10) Patent No.: US 12,410,413 B2
(45) Date of Patent: Sep. 9, 2025

(54) TRANSAMINASE MUTANT AND USE THEREOF

(71) Applicant: ASYMCHEM LABORATORIES (TIANJIN) CO., LTD., Tianjin (CN)

(72) Inventors: Hao Hong, Morrisville, NC (US); Gage James, Morrisville, NC (US); Yi Xiao, Tianjin (CN); Yulei Ma, Tianjin (CN); Na Zhang, Tianjin (CN); Xuecheng Jiao, Tianjin (CN); Huiyan Mu, Tianjin (CN); Yibing Cheng, Tianjin (CN); Shan Cao, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 553 days.

(21) Appl. No.: 17/769,204

(22) PCT Filed: Oct. 28, 2019

(86) PCT No.: PCT/CN2019/113743
§ 371 (c)(1),
(2) Date: Apr. 14, 2022

(87) PCT Pub. No.: WO2021/081713
PCT Pub. Date: May 6, 2021

(65) Prior Publication Data
US 2023/0227797 A1    Jul. 20, 2023

(51) Int. Cl.
*C12N 9/10* (2006.01)
*C12P 13/00* (2006.01)

(52) U.S. Cl.
CPC .......... *C12N 9/1096* (2013.01); *C12P 13/001* (2013.01)

(58) Field of Classification Search
None
See application file for complete search history.

(56) References Cited

U.S. PATENT DOCUMENTS 11,359,219 B2 * 6/2022 Hong ................. C12P 17/12
2020/0239895 A1   7/2020 Hong et al.

FOREIGN PATENT DOCUMENTS

| CN | 105765592 A | 7/2016 |
|---|---|---|
| CN | 107828751 A | 3/2018 |
| CN | 108048419 A | 5/2018 |
| CN | 108384767 A | 8/2018 |
| CN | 110205310 A | 9/2019 |
| EP | 3085776 A1 | 10/2016 |
| EP | 3733689 A1 | 11/2020 |
| WO | 2019095161 A1 | 5/2019 |
| WO | 2019148494 A1 | 8/2019 |

OTHER PUBLICATIONS

Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
International Search Report issued in connection with PCT Application No. PCT/CN2019/113743 dated Aug. 11, 2020.
Dawid Deszcz, et al. "Single active-site mutants are sufficient to enhance serine: pyruvate a-transaminase activity in as o-transaminase", the FEBS Journal 282, Apr. 1, 2015.

* cited by examiner

*Primary Examiner* — Christian L Fronda
(74) *Attorney, Agent, or Firm* — Dennemeyer & Associates LLC

(57) ABSTRACT

Provided are a transaminase mutant and use thereof. The transaminase mutant has an amino acid sequence obtained by mutation of an amino acid sequence shown in SEQ ID NO:1, the mutation at least includes one of the following mutation site combinations: T7C+S47C, Q78C+A330C, V137C+G313C, A217C+Y252C and L295C+C328C; or the transaminase mutant has an amino acid sequence which has the mutation sites in the mutated amino acid sequence and has 80% or more identity with the mutated amino acid sequence. The transaminase mutant realizes the change of protein structure and functions, reduces the enzyme amount, increases the enantiomeric excess (ee) value of a product, and reduces the difficulty of post-processing, so that the transaminase mutant may be suitable for industrial production.

20 Claims, No Drawings
Specification includes a Sequence Listing.

TRANSAMINASE MUTANT AND USE THEREOF

CROSS-REFERENCE TO RELATED APPLICATIONS

This is a 35 U.S.C. 371 National Stage Patent Application of International Application No. PCT/CN2019/113743, filed Oct. 28, 2019, which is hereby incorporated by reference in its entirety.

TECHNICAL FIELD

The present disclosure relates to the field of biotechnologies, in particular to transaminase mutants and use thereof.

BACKGROUND

Chiral amine compounds are key intermediates for the synthesis of many chiral drugs. Many important neurological drugs, cardiovascular drugs, antihypertensive drugs, anti-infective drugs and the like are synthesized by using a chiral amine as an intermediate. At present, the synthesis of the chiral amine is mainly achieved through chemical methods, such as asymmetric reduction of Schiff base (Chiral amine synthesis: methods, developments and applications [M]. West Sussex, United Kingdom: John Wiley & Sons. 2010), but there are disadvantages in reactions, such as harsh reaction conditions, use of toxic transition metal catalysts, and low product stereoselectivity.

A transaminase may catalyze the transfer of an amino group on an amino donor to a prochiral acceptor ketone, as to obtain the chiral amine and a by-product ketone. Because the transaminase has the advantages of high selectivity, high conversion rate and mild reaction conditions, it is widely used in the synthesis of the chiral amine. People already use an enzymatic method (Biocatalytic Asymmetric Synthesis of Chiral Amines from Ketones Applied to Sitagliptin Manufacture[J]. Science, 2010,329(5989):305-309.) or a chemical-enzymatic method to prepare many important chiral amines (Chemoenzymatic asymmetric total synthesis of (S)-Rivastigmine using omega-transaminases[J]. Cheminform, 2010, 46(30):5500-5502). However, in the industrial application and production, most of the wild transaminases have the disadvantages of low catalytic efficiency, poor stereoselectivity, and weak stability, so that there are not many transaminases that may really be used.

CN108048419A discloses a w-transaminase mutant F89Y+A417S derived from *Chromobacterium violaceum*, the mutant may catalyze dihydroxy ketal compounds to obtain a chiral ammonia product with the higher selectivity, and a reaction is as follows:

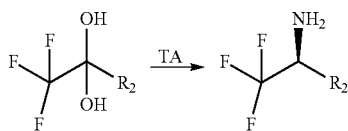

Herein, $R_2$=unsubstituted or substituted with one or more groups of an alkyl, an aralkyl or an aryl.

However, the activity thereof is low, and the amount of an enzyme added during the reaction is relatively large.

SUMMARY

The present disclosure aims to provide a transaminase mutant and use thereof, as to improve the activity of a transaminase.

In order to achieve the above purpose, according to one aspect of the present disclosure, a transaminase mutant is provided. The transaminase mutant has an amino acid sequence obtained by mutation of an amino acid sequence shown in SEQ ID NO:1, the mutation at least includes one of the following mutation site combinations: T7C+S47C, Q78C+A330C, V137C+G313C, A217C+Y252C and L295C+C328C; or the transaminase mutant has an amino acid sequence which has the mutation sites in the mutated amino acid sequence and has 80% or more identity with the mutated amino acid sequence.

Further, the mutation includes T7C+S47C and at least one of the following mutation sites: Q78, A330, V137, G313, A217, Y252, L295, C328, F22, A33, V42, A57, F89, N151, S156, M166, Y168, E171, K249, L283, S292, A299P, A334, F367, H369, V379, Q380, D396, F397, I400, C404, R405, F409, I414, R416, G419, S424, D436, R444 or G457.

Further, the mutation includes T7C+S47C and at least one of the following mutation sites: Q78C, V137C, G313C, F22P, A33V, A57V/Y, F89A/EV, N151A/E/F/Q/SV/W/Y, S156A/P/Q, M166A/D/E/F/G/K/S/W/Y, Y168A/E/l/M/SV, E171A/T, K249F, L283K, S292A, A299P, A33C, A334L/W, F367G/Q, H369A, V379A/D/L/V, Q380L, D396G/P/Y, F397K/Q/S/Y, I400P, C404Q/V, R405F, F409A/C/H/M/Q/T/V, I414Q, R416A/D/F/M/P/Q/S/TV, G419W, S424A/C/Q/LV, D436V/A, R444A/P/Y or G457C/P/W.

Further, the mutation includes at least one of the following mutation site combinations: T7C+S47C+D436A, T7C+S47C+Q380L+V379L, T7C+S47C+N151W or T7C+S47C+M166F.

Further, the mutation includes at least one of the following mutation site combinations: T7C+S47C+Q380L+V379L, T7C+S47C+Q380L+V379D, T7C+S47C+Q380L+V379A, T7C+S47C+Q380L+V379V, T7C+S47C+Q78C+A330C+Y89A, T7C+S47C+Q78C+A330C+Y89E, T7C+S47C+V137C+G313C+Y89V, T7C+S47C+Q380L+V379L+S156P, T7C+S47C+Q78C+A330C+S156Q, T7C+S47C+K249F+I400P+S156A, T7C+S47C+Q380L+V379L+M166F, T7C+S47C+H369A+C404V+M166A, T7C+S47C+H369A+F22P+M166V, T7C+S47C+H369A+L283K+M166S, T7C+S47C+A33V+A57Y+M166Y, T7C+S47C+A33V+A57V+M166G, T7C+S47C+Q380L+V379L+M166F+S424A, T7C+S47C+A33V+A57V+M166Y+S424G, T7C+S47C+Q380L+V379L+F397K+S424L, T7C+S47C+Q380L+V379L+M166F+R416T, T7C+S47C+S292A+A299P+M166K+R416T, T7C+S47C+S292A+A299P+M166F+R416P, T7C+S47C+S292A+A299P+M166F+R416D, T7C+S47C+Q380L+V379L+M166F+Y168I, T7C+S47C+Q380L+V379L+M166F+Y168M, T7C+S47C+S292A+A299P+M166E+Y168A, T7C+S47C+A334L+F367G+M166S+Y168V, T7C+S47C+Q380L+V379L+M166F+N151Q, T7C+S47C+Q380L+V379L+M166F+N151W, T7C+S47C+A334W+F367Q+M166F+N151S, T7C+S47C+Q380L+V379L+M166F+N151Y, T7C+S47C+Q380L+V379L+M166F+R416D, T7C+S47C+Q380L+V379L+M166F+R416P, T7C+S47C+Q380L+V379L+M166F+R416D+I414Q, T7C+S47C+D436A+R457W+M166F+R416D+R444A, T7C+S47C+D436A+R444P+M166S+R416F+D436V, T7C+S47C+D436A+R444Y+M166S+R416F+G419W, T7C+S47C+Q380L+V379L+M166F+R416D+N151W, T7C+S47C+Q380L+V379L+M166F+R416D+N151F, T7C+S47C+D436A+R457C+M166E+R416Q+N151A, T7C+S47C+D436A+R457P+M166W+R416F+N151V, T7C+S47C+D436A+V379L+M166F+R416D+N151E, T7C+S47C+Q380L+V379L+M166F+R416D+Y168E, T7C+S47C+D396Y+F397Q+M166F+R416D+Y168M, T7C+S47C+D396P+

F397S+M166G+R416S+Y168S, T7C+S47C+Q380L+ V379L+M166F+R416D+Y168A, T7C+S47C+Q380L+ V379L+M166F+R416D+N151W+Y168M, T7C+S47C+ D396G+F397Y+M166F+R416D+N151W+Y168A, T7C+ S47C+D396G+F397Y+M166D+R416F+N151W+Y168S, T7C+S47C+D396G+F397Y+M166D+R416D+N151W+ Y168E, T7C+S47C+Q380L+V379L+M166F+R416D+ N151W+S424C, T7C+S47C+Q380L+V379L+M166F+ R416D+N151W+S424A, T7C+S47C+Q380L+V379L+ M166F+R416D+N151W+S424V, T7C+S47C+Q380L+ V379L+M166F+R416D+N151W+F409Q, T7C+S47C+ Q380L+V379L+M166F+R416D+N151W+F409V, T7C+ S47C+Q380L+V379L+M166F+R416D+N151W+F409H, T7C+S47C+Q380L+V379L+M166F+R416D+N151W+ F409M, T7C+S47C+Q380L+V379L+M166F+R416D+ N151W+F409T. T7C+S47C+Q380L+V379L+M166F+ R416D+N151W+F409A, T7C+S47C+D396G+F397Y+ M166A+R416V+N151W+F409M, T7C+S47C+D396G+ F397Y+M166A+R416V+N151W+F409T, T7C+S47C+ D396G+F397Y+M166A+R416V+N151W+F409A, T7C+ S47C+Q380L+V379L+M166F+R416D+N151W+S424V+ F409C, T7C+S47C+Q380L+V379L+M166F+R416D+ N151W+S424A+F409Q, T7C+S47C+Q380L+V379L+ M166F+R416D+N151W+S424A+F409C, T7C+S47C+ Q380L+V379L+M166F+R416D+N151W+F409H+E171T, T7C+S47C+Q380L+V379L+M166F+R416D+N151W+ F409H+E171A, T7C+S47C+C404Q+R405F+M166S+ R416D+N151W+S424V+F409C, T7C+S47C+C404Q+ R405F+M166E+R416M+N151W+S424A+F409Q, T7C+ S47C+C404Q+R405F+M166S+R416A+N151W+S424A+ F409C, T7C+S47C+C404Q+R405F+M166T+R416A+ N151W+F409H+E171T, or T7C+S47C+C404Q+R405F+ M166Y+R416A+N151W+F409H+E171A.

According to another aspect of the present disclosure, a DNA molecule is provided. The DNA molecule encodes the above transaminase mutant.

According to another aspect of the present disclosure, a recombinant plasmid is provided. The recombinant plasmid contains the above DNA molecule.

Further, the recombinant plasmids are pET-22a(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the present disclosure, a host cell is provided. The host cell contains the above recombinant plasmid.

Further, the host cells include a prokaryotic cell, yeast or a eukaryotic cell; preferably the prokaryotic cell is an *E. coli* BL21-DE3 cell or an *E. coli* Rosetta-DE3 cell.

According to another aspect of the present disclosure, a method for producing a chiral amine is provided. The method includes a step of catalyzing a transamination reaction of a ketone compound and an amino donor by a transaminase, and the transaminase is any one of the above transaminase mutants.

Further, the ketone compound is

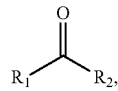

and a product of the transamination reaction is

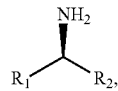

herein, $R_1$ and $R_2$ each independently represent an optionally substituted or unsubstituted alkyl, an optionally substituted or unsubstituted aralkyl, or an optionally substituted or unsubstituted aryl; the $R_1$ and $R_2$ may be singly or combined with each other to form a substituted or unsubstituted ring; preferably, the ketone compound is a dihydroxy ketal compound, and the reaction is a transamination reaction for generating

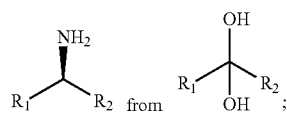

preferably, the $R_1$ and $R_2$ are an optionally substituted or unsubstituted alkyl having 1~20 carbon atoms, an optionally substituted or unsubstituted aralkyl, or an optionally substituted or unsubstituted aryl, more preferably an optionally substituted or unsubstituted alkyl having 1~10 carbon atoms, an optionally substituted or unsubstituted aralkyl, or an optionally substituted or unsubstituted aryl; preferably, the substitution refers to substitution by a halogen atom, a nitrogen atom, a sulfur atom, a hydroxyl, a nitro group, a cyano group, a methoxy, an ethoxy, a carboxyl, a carboxymethyl, a carboxyethyl or a methylenedioxy; preferably, the $R_1$ represents a methyl or a halogen-substituted methyl, more preferably, the halogen-substituted methyl is $CF_3$, $CF_2H$, $CCl_3$, $CCl_2H$, $CBr_3$ or $CBr_2H$, and more preferably, $CF_3$ or $CF_2H$; and preferably, the ketone compound is

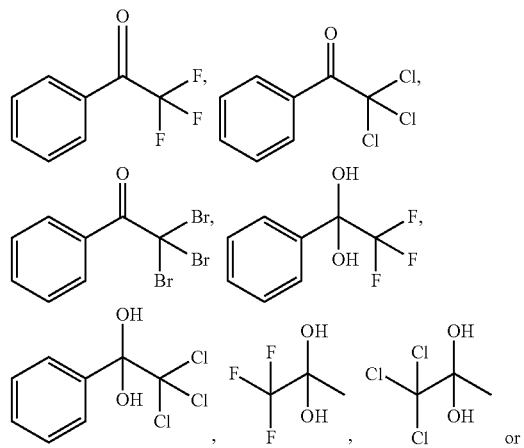

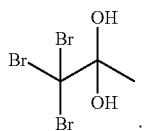

Further, the amino donor is isopropylamine or alanine, preferably isopropylamine.

Further, in a reaction system in which the transaminase catalyzes the transamination reaction of the ketone compound and the amino donor, a pH is 7~11, preferably 8~10, more preferably 9~10; preferably, the temperature of the reaction system for catalyzing the transamination reaction of the ketone compound and the amino donor by the transaminase is 25° C.~60° C., more preferably 30~55° C., and further preferably 40~50° C.; and preferably, the volume concentration of dimethyl sulfoxide in the reaction system for catalyzing the transamination reaction of the ketone compound and the amino donor by the transaminase is 0%~50%, more preferably 0%~20%.

The above transaminase mutant of the present disclosure is based on the w-transaminase mutant F89Y+A417S derived from *Chromobacterium violaceum* shown in SEQ ID NO:1, and is mutated by a method of site-directed mutagenesis, thereby the amino acid sequence thereof is changed, the change of protein structure and functions is achieved, the amount of the enzyme used is reduced, the ee value of the product is improved, and the difficulty of post-processing is reduced, so that it may be suitable for the industrial production.

DETAILED DESCRIPTION OF THE EMBODIMENTS

It should be noted that embodiments in the present application and features in the embodiments may be combined with each other in the case without conflicting. The present disclosure is described in detail below in combination with the embodiments.

The activity of a wild enzyme is lower, and the amount of an enzyme used is relatively large. In order to solve the above problems, the present disclosure uses a means of directed evolution to perform protein modification on the wild enzyme, as to improve the activity and stereoselectivity of the enzyme, and develop a transaminase that may be used in the industrial production.

The inventor evolves a mutant SEQ ID NO: 1 (Publication number CN108048419A) of a w-transaminase derived from *Chromobacterium violaceum* by the method of the directed evolution, the enzyme activity is improved, the amount of the enzyme used is reduced, and the stereoselectivity of the enzyme is further improved.

Specifically, the w-transaminase mutant F89Y+A417S (SEQ ID NO:1) derived from *Chromobacterium violaceum* is used as a template (in the present disclosure, "F89Y" is taken as an example, it means "original amino acid+site+mutated amino acid", namely F in the 89-th site is changed into Y). Firstly, 10 pairs of site-directed mutagenesis primers are designed, and 5 pairs of double-site combination mutations (T7C+S47C, Q78C+A330C, V137C+G313C, A217C+Y252C, L295C+C328C) are constructed to improve the reactivity of the enzyme under a high temperature condition. The site-directed mutagenesis is used, and pET-22b(+) is used as an expression vector, as to obtain a mutant plasmid with a target gene.

Site-directed mutagenesis: refers to the introduction of a desired change (usually a change representing a favorable direction) into a target DNA fragment (may be a genome or a plasmid) by a polymerase chain reaction (PCR) and other methods, including addition of bases, deletion, point mutation and the like. The site-directed mutagenesis may quickly and efficiently improve the properties and representation of the target protein expressed by the DNA, and it is a very useful method in the gene research.

A method of introducing site-directed mutation by using a whole-plasmid PCR is simple and effective, and is currently a more commonly used method. A principle thereof is that a pair of primers (forward and reverse) containing mutation sites are annealed with a template plasmid, and then "circularly extended" with a polymerase. The so-called cyclic extension means that the polymerase extends the primers according to the template and returns to 5'-end of the primer after a circle, and then it undergoes a cycle of repeated heating and annealing and extending. This reaction is different from rolling circle amplification, and does not form a plurality of tandem copies. Extension products of the forward and reverse primers are annealed and matched to form an open-circle plasmid with a nick. The template DNA derived from a dam+ strain may be recognized and digested by a DpnI enzyme because it has a methylation site. However, the plasmid with a mutant sequence synthesized in vitro is not digested because it is not methylated, and the nick may be naturally repaired after being transformed into *E. coli*, so a clone with the mutant plasmid may be obtained. The mutant plasmid is transformed into an *E. coli* competent cell, spread on a culture dish containing an LB solid medium (100 μg/mL ampicillin), and cultured overnight at 37° C. The single clones grown on the solid medium are activated. After the sequence identification, the expression of the transaminase is induced overnight under conditions of 0.2 mM isopropyl-p-d-thiogalactoside (IPTG) at 25° C. Then, crude enzyme solution is obtained by methods of centrifugation and ultrasonic breaking of cells, and is used for the detection of reaction characteristics.

A computer is used to perform docking simulation analysis on a three-dimensional structure of the transaminase and a substrate, some amino acids near an enzyme catalytic center are selected, and may have a great relationship with the enzyme activity. On the basis of the constructed double-site mutation, a saturation mutation is performed on these potentially influential amino acid sites. 31 pairs of saturation mutation primers (F22, A33, V42, A57, F89, N151, S156, M166, Y168, E171, K249, L283, S292, A299, A334, F367, H369, V379&Q380L, D396, F397, I400, C404, R405, F409, I414, R416, G419, S424, D436, R444, G457) are designed, as to obtain the mutant with the greatly improved activity.

Herein, the saturation mutation is a method to obtain a mutant in which an amino acid in a target site is replaced by 19 other amino acids in a short time by modifying a coding gene of a target protein. This method is not only a powerful tool for directed modification of the protein, but also an important method for the study of a protein structure-function relationship. The saturation mutation may often obtain a more ideal evolutionary body than single-site mutation. For these problems that the site-directed mutation method may not solve, it is precisely a unique point that the saturation mutation method is good at.

On the basis of the mutant with the increased activity obtained by the saturation mutation, beneficial amino acid sites may be combined, as to obtain the mutant with the better characters. A construction method for the double-site mutation in combined mutations is the same as a construction method for the single-site mutation, and it is constructed by using the whole plasmid PCR method. Multi-site mutation for simultaneously mutating two or more sites is performed by using overlap extension PCR amplification, as to obtain a mutated gene containing the multi-site mutation. After two ends thereof are digested with a restriction enzyme, it is connected to the expression vector, and transformed into the *E. coli* cell, spread on the LB culture dish containing 100 μg/mL ampicillin, and cultured overnight at 37° C., as to obtain the combined mutant, which is identified by sequencing.

Gene splicing by overlap extension PCR (referred to as SOEPCR) uses a primer with complementary ends to form an overlap strand of a PCR product, so that in a subsequent amplification reaction, the overlap strand is extended to overlap and splice amplification fragments from different sources. This technology uses a PCR technology to perform effective gene recombination in vitro, and is often used in the construction of multi-site mutation.

According to a typical embodiment of the present disclosure, a transaminase mutant is provided. An amino acid sequence of the transaminase mutant is an amino acid sequence obtained by mutation of an amino acid sequence shown in SEQ ID NO: 1 (MQKQRTTSQWREL-DAAHHLHPFTDTASLNQAGARVMTRGEGVYLWD-SEGNKIIDGMAGLWCVN VGYGRKDFAEAARRQ-MEELPFYNTFYKTTHPAVVELSSLLAEVTPAGFDR-VFYTNSGSESVDTMIR MVRRYWDVQGKPEKKTLI-GRWNGYHGSTIGGASLGGMKYMHEQGDLPIPGMA-HIEQPWWYKH GKDMTPDEFGVVAARWLEEKILE-IGADKVAAFVGEPIQGAGGVIVPPATYWPEIERICRK-YDVLLVA DEVICGFGRTGEWFGHQHFGFQPDLFT-AAKGLSSGYLPIGAVFVGKRVAEGLIAGGDFNHGF-TYS GHPVCAAVAHANVAALRDEGIVQRVKDDIGPY-MQKRWRETFSRFEHVDDVRGVGMVQAFTLVKN KAKRELFPDFGEIGTLCRDIFFRNNLIMRSCG-DHIVSAPPLVMTRAEVDEMLAVAERCLEEFEQTLK ARGLA), the mutation include at least one of the following mutation site combinations: T7C+S47C, Q78C+A330C, V137C+G313C, A217C+Y252C and L295C+C328C; or the transaminase mutant has an amino acid sequence which has the mutation sites in the mutated amino acid sequence and has 80% or more identity with the mutated amino acid sequence.

The above transaminase mutant of the present disclosure is based on the w-transaminase mutant F89Y+A417S derived from *Chromobacterium violaceum* shown in SEQ ID NO:1, and is mutated by a method of site-directed mutagenesis, thereby the amino acid sequence thereof is changed, the change of protein structure and functions is achieved, the amount of the enzyme used is reduced, the ee value of the product is improved, and the difficulty of post-processing is reduced, so that it may be suitable for the industrial production.

A term "identity" used herein has the meaning generally known in the field, and those skilled in the art are also familiar with rules and standards for determining the identity between different sequences. The sequence defined by the present disclosure with different degrees of the identity must also have an increase in transaminase activity. In the above embodiment, preferably the amino acid sequence of the transaminase mutant has the above identity and has or encodes the amino acid sequence with the increased activity. Those skilled in the art may obtain such a variant sequence under the teaching of the disclosure of the present application.

Preferably, the mutation includes T7C+S47C and at least one of the following mutation sites: Q78, A330, V137, G313, A217, Y252, L295, C328, F22, A33, V42, A57, F89, N151, S156, M166, Y168, E171, K249, L283, S292, A299P, A334, F367, H369, V379, Q380, D396, F397, I400, C404, R405, F409, I414, R416, G419, S424, D436, R444, G457.

More preferably, the mutation includes T7C+S47C and at least one of the following mutation sites: Q78C, V137C, G313C, F22P, A33V, A57V/Y, F89A/EV, N151A/E/F/Q/S/V/W/Y, S156A/P/Q, M166A/D/E/F/G/K/S/W/Y, Y168A/E/I/M/SV, E171A/T, K249F, L283K, S292A, A299, A33C, A334L/W, F367G/Q, H369A, V379A/D/L/V, Q380L, D396G/P/Y, F397K/Q/S/Y, I400P, C404Q/V, R405F, F409A/C/H/M/Q/TV, I414Q, R416A/D/F/M/P/Q/S/TV, G419W, S424A/C/Q/LV, D436V/A, R444A/P/Y and G457C/P/W. Herein, "/" stands for "or".

More preferably, the mutations include at least one of the following mutation site combinations: T7C+S47C+S292A, T7C+S47C+D436A, T7C+S47C+D396G, T7C+S47C+Q380L, T7C+S47C+A299P, T7C+S47C+F397Y, T7C+S47C+S424A, T7C+S47C+V379L, T7C+S47C+M166F, T7C+S47C+M166A, T7C+S47C+R405F T7C+S47C+R416V, T7C+S47C+R416D, T7C+S47C+R416A, T7C+S47C+N151W, T7C+S47C+C404Q+R405F, T7C+S47C+Q78C+A330C, T7C+S47C+Q380L+V379L, T7C+S47C+Q380L+R416D, T7C+S47C+V379L+N151W, T7C+S47C+Q380L+V379L+M166F, T7C+S47C+C404Q+R405F+M166F+R416A+N151W and T7C+S47C+Q380L+V379L+M166F+R416D+N151W.

Further preferably, the mutation includes at least one of the following mutation site combinations: T7C+S47C+Q380L+V379L, T7C+S47C+Q380L+V379D, T7C+S47C+Q380L+V379A, T7C+S47C+Q380L+V379V, T7C+S47C+Q78C+A330C+Y89A, T7C+S47C+Q78C+A330C+Y89E, T7C+S47C+V137C+G313C+Y89V, T7C+S47C+Q380L+V379L+S156P, T7C+S47C+Q78C+A330C+S156Q, T7C+S47C+K249F+I400P+S156A, T7C+S47C+Q380L+V379L+M166F, T7C+S47C+H369C+A404V+M166A, T7C+S47C+H369A+F22P+M166V, T7C+S47C+H369A+L283K+M166S, T7C+S47C+A33V+A57Y+M166Y, T7C+S47C+A33V+A57V+M166G, T7C+S47C+Q380L+V379L+M166F+S424A, T7C+S47C+A33V+A57V+M166Y+S424G, T7C+S47C+Q380L+V379L+F397K+S424L, T7C+S47C+Q380L+V379L+M166F+R416T, T7C+S47C+S292A+A299P+M166K+R416T, T7C+S47C+S292A+A299P+M166F+R416P, T7C+S47C+S292A+A299P+M166F+R416D. T7C+S47C+Q380L+V379L+M166F+Y168I, T7C+S47C+Q380L+V379L+M166F+Y168M, T7C+S47C+S292A+A299P+M166E+Y168A, T7C+S47C+A334L+F367G+M166S+Y168V, T7C+S47C+Q380L+V379L+M166F+N151Q, T7C+S47C+Q380L+V379L+M166F+N151W, T7C+S47C+A334W+F367Q+M166F+N151 S, T7C+S47C+Q380L+V379L+M166F+N151Y, T7C+S47C+Q380L+V379L+M166F+R416D, T7C+S47C+Q380L+V379L+M166F+R416P, T7C+S47C+Q380L+V379L+, M166F+R416D+I414Q, T7C+S47C+D436A+R457W+M166F+R416D+R444A, T7C+S47C+D436A+R444P+M166S+R416F+D436V, T7C+S47C+D436A+R444Y+M166S+R416F+G419W, T7C+S47C+Q380L+V379L+M166F+R416D+N151W, T7C+S47C+Q380L+V379L+M166F+R416D+N151F, T7C+S47C+D436A+R457C+M166E+R416Q+N151A, T7C+S47C+D436A+R457P+M166W+R416F+N151V, T7C+S47C+D436A+V379L+M166F+R416D+N151E, T7C+S47C+

Q380L+V379L+M166F+R416D+Y168E, T7C+S47C+ D396Y+F397Q+M166F+R416D+Y168M, T7C+S47C+ D396P+F397S+M166G+R416S+Y168S, T7C+S47C+ Q380L+V379L+M166F+R416D+Y168A, T7C+S47C+ Q380L+V379L+M166F+R416D+N151W+Y168M, T7C+ S47C+D396G+F397Y+M166F+R416D+N151W+Y168A, T7C+S47C+D396G+F397Y+M166D+R416F+N151W+ Y168S, T7C+S47C+D396G+F397Y+M166D+R416D+ N151W+Y168E, T7C+S47C+Q380L+V379L+M166F+ R416D+N151W+S424C, T7C+S47C+Q380L+V379L+ M166F+R416D+N151W+S424A, T7C+S47C+Q380L+ V379L+M166F+R416D+N151W+S424V, T7C+S47C+ Q380L+V379L+M166F+R416D+N151W+F409Q, T7C+ S47C+Q380L+V379L+M166F+R416D+N151W+F409V, T7C+S47C+Q380L+V379L+M166F+R416D+N151W+ F409H, T7C+S47C+Q380L+V379L+M166F+R416D+ N151W+F409M, T7C+S47C+Q380L+V379L+M166F+ R416D+N151W+F409T, T7C+S47C+Q380L+V379L+ M166F+R416D+N151W+F409A, T7C+S47C+D396G+ F397Y+M166A+R416V+N151W+F409M, T7C+S47C+ D396G+F397Y+M166A+R416V+N151W+F409T, T7C+ S47C+D396G+F397Y+M166A+R416V+N151W+F409A, T7C+S47C+Q380L+V379L+M166F+R416D+N151W+ S424V+F409C, T7C+S47C+Q380L+V379L+M166F+ R416D+N151W+S424A+F409Q, T7C+S47C+Q380L+ V379L+M166F+R416D+N151W+S424A+F409C, T7C+ S47C+Q380L+V379L+M166F+R416D+N151W+F409H+ E171T, T7C+S47C+Q380L+V379L+M166F+R416D+ N151W+F409H+E171A, T7C+S47C+C404Q+R405F+ M166S+R416D+N151W+S424V+F409C, T7C+S47C+ C404Q+R405F+M166E+R416M+N151W+S424A+F409Q, T7C+S47C+C404Q+R405F+M166S+R416A+N151W+ S424A+F409C, T7C+S47C+C404Q+R405F+M166T+ R416A+N151W+F409H+E171T, and T7C+S47C+C404Q+ R405F+M166Y+R416A+N151W+F409H+E171A.

According to a typical embodiment of the present disclosure, a DNA molecule is provided. The DNA molecule encodes the above transaminase mutant. The above transaminase mutant encoded by the DNA molecule has high soluble expression characteristics and high activity characteristics.

The above DNA molecule of the present disclosure may also exist in the form of an "expression cassette". The "expression cassette" refers to a linear or circular nucleic acid molecule, covering DNA and RNA sequences that may direct the expression of a specific nucleotide sequence in an appropriate host cell. Generally speaking, it includes a promoter operatively linked to a target nucleotide, and it is optionally operatively linked to a termination signal and/or other regulatory elements. The expression cassette may also include a sequence required for proper translation of the nucleotide sequence. A coding region usually encodes a target protein, but also encodes a target functional RNA in a sense or antisense direction, such as an antisense RNA or an untranslated RNA. The expression cassette containing a target polynucleotide sequence may be chimeric, it means that at least one of components thereof is heterologous to at least one of the other components. The expression cassette may also be naturally existent, but obtained by efficient recombination for heterologous expression.

According to a typical embodiment of the present disclosure, a recombinant plasmid is provided. The recombinant plasmid contains any one of the above DNA molecules. The DNA molecule in the above recombinant plasmid is placed in an appropriate position of the recombinant plasmid, so that the DNA molecule may be replicated, transcribed or expressed correctly and smoothly.

Although a qualifier used in the present disclosure to define the above DNA molecule is "containing", it does not mean that other sequences that are not related to functions thereof may be arbitrarily added to both ends of the DNA sequence. Those skilled in the art know that in order to meet the requirements of a recombination operation, it is necessary to add suitable restriction endonuclease cleavage sites at both ends of the DNA sequence, or to additionally add a start codon, a stop codon and the like, therefore, if the closed expression is used to define, these situations may not be truly covered.

A term "plasmid" used in the present disclosure includes any plasmids, cosmids, bacteriophages or *agrobacterium* binary nucleic acid molecules in double-stranded or single-stranded linear or circular form, preferably a recombinant expression plasmid, it may be a prokaryotic expression plasmid, or a eukaryotic expression plasmid, but preferably the prokaryotic expression plasmid. In some embodiments, the recombinant plasmid is selected from pET-22a(+), pET-22b(+), pET-3a(+), pET-3d(+), pET-11a(+), pET-12a(+), pET-14b(+), pET-15b(+), pET-16b(+), pET-17b(+), pET-19b (+), pET-20b(+), pET-21a(+), pET-23a(+), pET-23b(+), pET-24a(+), pET-25b(+), pET-26b(+), pET-27b(+), pET-28a (+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant plasmid is pET-22b(+).

According to a typical embodiment of the present disclosure, a host cell is provided. The host cell contains any one of the above recombinant plasmids. The host cell suitable for the present disclosure includes but is not limited to a prokaryotic cell, yeast or a eukaryotic cell. Preferably, the prokaryotic cell is eubacteria, for example gram-negative bacteria or gram-positive bacteria. More preferably, the prokaryotic cell is an *E. coli* BL21 cell or an *E. coli* DH5a competent cell.

According to a typical embodiment of the present disclosure, a method for producing a chiral amine is provided. The method includes a step of catalyzing a transamination reaction of a ketone compound and an amino donor by a transaminase, and the transaminase is any one of the above transaminase mutants resistant to an organic solvent. Since the above transaminase mutant of the present disclosure has good catalytic activity and specificity, the chiral amine prepared by the transaminase mutant of the present disclosure may increase the reaction rate, reduce the amount of the enzyme, and reduce the difficulty of post-processing.

Further, the ketone compound is

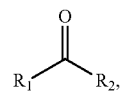

and a product of the transamination reaction is

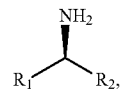

herein, $R_1$ and $R_2$ each independently represent an optionally substituted or unsubstituted alkyl, an optionally substituted or unsubstituted aralkyl, or an optionally substituted or unsubstituted aryl; the $R_1$ and $R_2$ may be singly or combined with each other to form a substituted or unsubstituted ring; preferably, the ketone compound is a dihydroxy ketal compound, and the reaction is a transamination reaction for generating

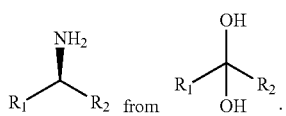

Preferably, the $R_1$ and $R_2$ are an optionally substituted or unsubstituted alkyl having 1~20 carbon atoms, an optionally substituted or unsubstituted aralkyl, or an optionally substituted or unsubstituted aryl, more preferably an optionally substituted or unsubstituted alkyl having 1~10 carbon atoms, an optionally substituted or unsubstituted aralkyl, or an optionally substituted or unsubstituted aryl.

Preferably, the substitution refers to substitution by a halogen atom, a nitrogen atom, a sulfur atom, a hydroxyl, a nitro group, a cyano group, a methoxy, an ethoxy, a carboxyl, a carboxymethyl, a carboxyethyl or a methylenedioxy.

Preferably, the $R_1$ represents a methyl or a halogen-substituted methyl, more preferably, the halogen-substituted methyl is $CF_3$, $CF_2H$, $CCl_3$, $CCl_2H$, $CBr_3$ or $CBr_2H$, and further preferably, $CF_3$ or $CF_2H$.

Preferably, the ketone compound is a dihydroxy ketal compound, and a transamination reaction formula is one of the following:

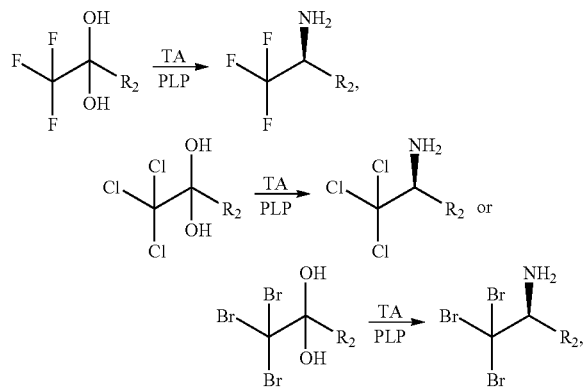

Herein, TA is a transaminase, and PLP is a pyridoxal phosphate.

In a typical embodiment of the present disclosure, the amino donor is isopropylamine or alanine, preferably isopropylamine.

In a reaction system in which the transaminase of the present disclosure is used to catalyze a transamination reaction of the ketone compound and the amino donor, a pH is 7~11, preferably 8~10, more preferably 9~10, it means that the value of the pH may be a value optionally selected from 7~11, for example 7, 7.5, 8, 8, 8.6, 9, 10, 10.5 and the like. The temperature of the reaction system in which the transaminase catalyzes the transamination reaction of the ketone compound and the amino donor is 25~60° C., more preferably 30~55° C., further preferably 40~50° C., in other words, the value of the temperature may be a value optionally selected from 25~60° C., for example 30, 31, 32, 35, 37, 38, 39, 40, 42, 45, 48, 50, 51, 52, 55 and the like. The volume concentration of dimethyl sulfoxide in the reaction system in which the transaminase catalyzes the transamination reaction of the ketone compound and amino donor is 0%~50%, for example 10%, 15%, 18%, 20%, 30%, 35%, 38%, 40%, 42%, 48%, 49% and the like.

Those skilled in the art know that many modifications may be made to the present disclosure without departing from the spirit of the present disclosure, and such modifications also fall within a scope of the present disclosure. In addition, the following experimental methods are conventional methods unless otherwise specified, and experimental materials used may be easily obtained from commercial companies unless otherwise specified.

The beneficial effects of the present disclosure are further described below in combination with experimental data and the embodiments.

Embodiment 1

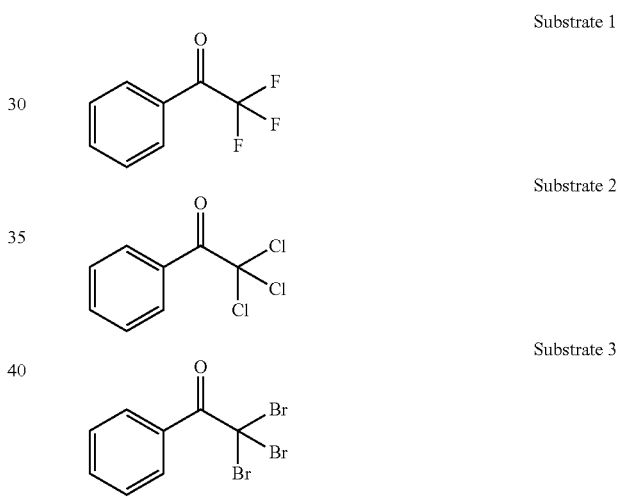

10 mg of substrate 1/substrate 2/substrate 3 is respectively dissolved in 30 μL of dimethylsulfoxide (DMSO) to prepare substrate solution. 10 mg of a transaminase, 66.6 μL of isopropylamine hydrochloride solution (6M), 0.1 mg of pyridoxal phosphate (PLP), and 0.1 M of Tris-CI buffer (pH 9.0) are successively added to a reaction system so as to make up to a total volume of 500 μL, and finally the prepared substrate solution is added, a pH is adjusted to 9.0, and it is reacted for 16 h at 200 rpm and 45° C. of a constant temperature. 2 times of acetonitrile in volume is added to the reaction system, fully mixed uniformly, standing for 10 min, and centrifuged at 12000 rpm for 10 min, a supernatant is taken, and it is sent to a liquid phase to measure the conversion rate after being diluted by 10 times. ee value detection method: 2 times of the acetonitrile in volume is added to the reaction system, fully mixed uniformly, standing for 10 min, and centrifuged at 12000 rpm for 10 min, a supernatant is taken, anhydrous $MgSO_4$ is added to remove water, it is centrifuged at 12000 rpm for 10 min, a supernatant is taken, $N_2$ is used to blow dry, 1 mL of methanol is added, and it is sent to the liquid phase for detection after being dissolved. The reaction characteristics of some mutants are shown in Table 1:

TABLE 1

| Mutant | Substrate 1 | | Substrate 2 | | Substrate 3 | |
|---|---|---|---|---|---|---|
| | Activity | ee value | Activity | ee value | Activity | ee value |
| Female parent | − | * | − | * | − | * |
| T7C + S47C | ++ | * | ++ | * | ++ | * |
| Q78C + A330C | ++ | ** | ++ | ** | ++ | ** |
| V137C + G313C | ++ | ** | ++ | ** | ++ | ** |
| A217C + Y252C | ++ | ** | ++ | ** | ++ | ** |
| L295C + C328C | ++ | ** | ++ | ** | ++ | ** |
| T7C + S47C + Q380L + V379L | +++ | ** | +++ | ** | ++ | ** |
| T7C + S47C + Q380L + V379D | ++ | ** | +++ | ** | ++ | ** |
| T7C + S47C + Q380L + V379A | +++ | ** | +++ | ** | ++ | ** |
| T7C + S47C + Q380L + V379V | +++ | ** | ++ | ** | ++ | ** |
| T7C + S47C + Q78C + A330C + Y89A | ++ | ** | +++ | ** | ++ | ** |
| T7C + S47C + Q78C + A330C + Y89E | +++ | ** | ++ | ** | ++ | ** |
| T7C + S47C + V137C + G313C + Y89V | +++ | ** | +++ | ** | +++ | ** |
| T7C + S47C + Q380L + V379L + S156P | +++ | ** | ++ | ** | ++ | ** |
| T7C + S47C + Q78C + A330C + S156Q | +++ | ** | ++ | ** | ++ | ** |
| T7C + S47C + K249F + I400P + S156A | +++ | ** | ++ | ** | ++ | ** |
| T7C + S47C + Q380L + V379L + M166F | ++++ | ** | +++ | ** | ++ | ** |
| T7C + S47C + H369A + C404V + M166A | +++ | ** | ++++ | ** | +++ | ** |
| T7C + S47C + H369A + F22P + M166V | ++++ | ** | +++ | ** | +++ | ** |
| T7C + S47C + H369A + L283K + M166S | +++ | ** | ++ | ** | +++ | ** |
| T7C + S47C + A33V + A57Y + M166Y | ++++ | ** | +++ | ** | +++ | ** |
| T7C + S47C + A33V + A57V + M166G | ++++ | ** | +++ | ** | +++ | ** |
| T7C + S47C + Q380L + V379L + M166F + S424A | ++++ | ** | ++++ | ** | +++ | ** |
| T7C + S47C + A33V + A57V + M166Y + S424G | +++ | ** | +++ | ** | +++ | ** |
| T7C + S47C + Q380L + V379L + F397K + S424L | ++ | ** | +++ | ** | ++ | ** |
| T7C + S47C + Q380L + V379L + M166F + R416T | ++++ | ** | ++++ | ** | ++++ | ** |
| T7C + S47C + S292A + A299P + M166K + R416T | +++ | ** | +++ | ** | +++ | ** |
| T7C + S47C + S292A + A299P + M166F + R416P | ++ | ** | +++ | ** | ++ | ** |
| T7C + S47C + S292A + A299P + M166F + R416D | ++++ | ** | +++ | ** | ++++ | ** |
| T7C + S47C + Q380L + V379L + M166F + Y168I | +++++ | ** | +++++ | ** | +++++ | ** |
| T7C + S47C + Q380L + V379L + M166F + Y168M | +++++ | ** | +++++ | ** | +++++ | ** |
| T7C + S47C + S292A + A299P + M166E + Y168A | ++++ | ** | +++ | ** | ++++ | ** |
| T7C + S47C + A334L + F367G + M166S + Y168V | +++ | ** | ++++ | ** | ++++ | ** |
| T7C + S47C + Q380L + V379L + M166F + N151Q | ++++ | ** | ++++ | ** | +++++ | ** |
| T7C + S47C + Q380L + V379L + M166F + N151W | ++++ | ** | ++++ | ** | ++++ | ** |
| T7C + S47C + A334W + F367Q + M166F + N151S | ++++ | ** | +++ | ** | ++++ | ** |
| T7C + S47C + Q380L + V379L + M166F + N151Y | ++++ | ** | +++ | ** | ++++ | ** |
| T7C + S47C + Q380L + V379L + M166F + R416D | ++++ | ** | ++++ | ** | +++ | ** |
| T7C + S47C + Q380L + V379L + M166F + R416P | ++++ | ** | +++ | ** | ++++ | ** |
| T7C + S47C + Q380L + V379L + M166F + R416D + I414Q | ++++ | ** | ++++ | ** | ++++ | ** |
| T7C + S47C + D436A + R457W + M166F + R416D + R444A | ++++ | ** | +++ | ** | ++++ | ** |
| T7C + S47C + D436A + R444P + M166S + R416F + D436V | +++ | ** | ++++ | ** | ++++ | ** |
| T7C + S47C + D436A + R444Y + M166S + R416F + G419W | ++++ | ** | ++++ | ** | ++++ | ** |
| T7C + S47C + Q380L + V379L + M166F + R416D + N151W | +++++ | ** | +++++ | ** | ++++ | ** |
| T7C + S47C + Q380L + V379L + M166F + R416D + N151F | +++++ | ** | +++++ | ** | +++++ | ** |
| T7C + S47C + D436A + R457C + M166E + R416Q + N151A | +++++ | ** | +++++ | ** | +++++ | ** |
| T7C + S47C + D436A + R457P + M166W + R416F + N151V | ++++ | ** | ++++ | ** | ++++ | ** |
| T7C + S47C + D436A + V379L + M166F + R416D + N151E | ++++ | ** | ++++ | ** | ++++ | ** |
| T7C + S47C + Q380L + V379L + M166F + R416D + Y168E | ++++ | ** | ++++ | ** | +++++ | ** |
| T7C + S47C + D396Y + F397Q + M166F + R416D + Y168M | ++++ | ** | ++++ | ** | +++++ | ** |
| T7C + S47C + D396P + F397S + M166G + R416S + Y168S | ++++ | ** | +++++ | ** | ++++ | ** |
| T7C + S47C + Q380L + V379L + M166F + R416D + Y168A | ++++ | ** | ++++ | ** | ++++ | ** |
| T7C + S47C + Q380L + V379L + M166F + R416D + N151W + Y168M | +++++ | ** | ++++ | ** | +++++ | ** |

TABLE 1-continued

| Mutant | Substrate 1 Activity | Substrate 1 ee value | Substrate 2 Activity | Substrate 2 ee value | Substrate 3 Activity | Substrate 3 ee value |
|---|---|---|---|---|---|---|
| T7C + S47C + D396G + F397Y + M166F + R416D + N151W + Y168A | +++++ | ** | +++++ | ** | +++++ | ** |
| T7C + S47C + D396G + F397Y + M166D + R416F + N151W + Y168S | ++++ | ** | +++++ | ** | ++++ | ** |
| T7C + S47C + D396G + F397Y + M166D + R416D + N151W + Y168E | ++++ | ** | +++++ | ** | ++++ | ** |
| T7C + S47C + Q380L + V379L + M166F + R416D + N151W + S424C | +++++ | ** | +++++ | ** | +++++ | ** |
| T7C + S47C + Q380L + V379L + M166F + R416D + N151W + S424A | +++++ | ** | +++++ | ** | +++++ | ** |
| T7C + S47C + Q380L + V379L + M166F + R416D + N151W + S424V | +++++ | ** | ++++ | ** | +++ | ** |
| T7C + S47C + Q380L + V379L + M166F + R416D + N151W + F409Q | +++++ | ** | +++++ | ** | +++++ | ** |
| T7C + S47C + Q380L + V379L + M166F + R416D + N151W + F409V | +++++ | ** | ++++ | ** | +++++ | ** |
| T7C + S47C + Q380L + V379L + M166F + R416D + N151W + F409H | +++++ | ** | ++++ | ** | +++ | ** |
| T7C + S47C + Q380L + V379L + M166F + R416D + N151W + F409M | +++++ | ** | +++++ | ** | +++ | ** |
| T7C + S47C + Q380L + V379L + M166F + R416D + N151W + F409T | +++++ | ** | ++++ | ** | +++++ | ** |
| T7C + S47C + Q380L + V379L + M166F + R416D + N151W + F409A | +++++ | ** | ++++ | ** | +++ | ** |
| T7C + S47C + D396G + F397Y + M166A + R416V + N151W + F409M | +++++ | ** | ++++ | ** | +++++ | ** |
| T7C + S47C + D396G + F397Y + M166A + R416V + N151W + F409T | +++++ | ** | +++++ | ** | +++++ | ** |
| T7C + S47C + D396G + F397Y + M166A + R416V + N151W + F409A | +++++ | ** | +++++ | ** | +++ | ** |
| T7C + S47C + Q380L + V379L + M166F + R416D + N151W + S424V + F409C | ++++ | ** | ++++ | ** | ++++ | ** |
| T7C + S47C + Q380L + V379L + M166F + R416D + N151W + S424A + F409Q | +++++ | ** | ++++ | ** | ++++ | ** |
| T7C + S47C + Q380L + V379L + M166F + R416D + N151W + S424A + F409C | ++++ | ** | ++++ | ** | +++++ | ** |
| T7C + S47C + Q380L + V379L + M166F + R416D + N151W + F409H + E171T | ++++ | ** | +++++ | ** | +++++ | ** |
| T7C + S47C + Q380L + V379L + M166F + R416D + N151W + F409H + E171A | +++++ | ** | +++++ | ** | +++++ | ** |
| T7C + S47C + C404Q + R405F + M166S + R416D + N151W + S424V + F409C | +++++ | ** | +++++ | ** | +++ | ** |
| T7C + S47C + C404Q + R405F + M166E + R416M + N151W + S424A + F409Q | ++++ | ** | +++++ | ** | +++ | ** |
| T7C + S47C + C404Q + R405F + M166S + R416A + N151W + S424A + F409C | ++++ | ** | +++++ | ** | +++ | ** |
| T7C + S47C + C404Q + R405F + M166T + R416A + N151W + F409H + E171T | +++++ | ** | +++++ | ** | ++++ | ** |
| T7C + S47C + C404Q + R405F + M166Y + R416A + N151W + F409H + E171A | +++++ | ** | +++++ | ** | ++++ | ** |

The multiple of an activity increase is expressed by +, + means 5-10 times of the increase, ++ means 10-20 times of the increase, +++ means 20-50 times of the increase, ++++ means 50-100 times of the increase, +++++ means more than 100 times of the increase; and * means the ee value is 95%-98%, and ** means the ee value is >98%.

Embodiment 2

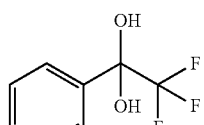

Substrate 4

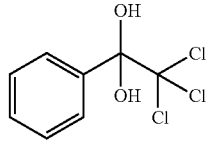

Substrate 5

10 mg of substrate 4/substrate 5 is respectively dissolved in 30 μL of DMSO to prepare substrate solution. 10 mg of a transaminase, 66.6 μL of isopropylamine hydrochloride solution (6M), 0.1 mg of PLP, and 0.1 M of Tris-Cl buffer (pH 9.0) are successively added to a reaction system so as to make up to a total volume of 500 μL, and finally the prepared substrate solution is added, a pH is adjusted to 9.0, and it is reacted for 16 h at 200 rpm and 45° C. of a constant temperature. 2 times of acetonitrile in volume is added to the reaction system, fully mixed uniformly, standing for 10 min, and centrifuged at 12000 rpm for 10 min, a supernatant is taken, and it is sent to a liquid phase to measure the conversion rate after being diluted by 10 times. ee value detection method: 2 times of the acetonitrile in volume is added to the reaction system, fully mixed uniformly, standing for 10 min, and centrifuged at 12000 rpm for 10 min, a supernatant is taken, anhydrous MgSO₄ is added to remove water, it is centrifuged at 12000 rpm for 10 min, a supernatant is taken, N₂ is used to blow dry, 1 mL of methanol is added, and it is sent to the liquid phase for detection after being dissolved. The reaction characteristics of some mutants are shown in Table 2:

TABLE 2

| Mutant | Substrate 4 Activity | Substrate 4 ee value | Substrate 5 Activity | Substrate 5 ee value |
|---|---|---|---|---|
| Female parent | − | * | − | * |
| T7C + S47C | ++ | * | ++ | * |
| Q78C + A330C | ++ | ** | ++ | ** |
| V137C + G313C | ++ | ** | ++ | ** |
| A217C + Y252C | ++ | ** | ++ | ** |
| L295C + C328C | ++ | ** | ++ | ** |
| T7C + S47C + Q380L + V379L | +++ | ** | +++ | ** |
| T7C + S47C + Q380L + V379D | ++ | ** | +++ | ** |
| T7C + S47C + Q380L + V379A | +++ | ** | +++ | ** |
| T7C + S47C + Q380L + V379V | +++ | ** | ++ | ** |
| T7C + S47C + Q78C + A330C + Y89A | ++ | ** | +++ | ** |
| T7C + S47C + Q78C + A330C + Y89E | +++ | ** | ++ | ** |
| T7C + S47C + V137C + G313C + Y89V | +++ | ** | +++ | ** |
| T7C + S47C + Q380L + V379L + S156P | +++ | ** | ++ | ** |
| T7C + S47C + Q78C + A330C + S156Q | +++ | ** | ++ | ** |
| T7C + S47C + K249F + I400P + S156A | +++ | ** | ++ | ** |
| T7C + S47C + Q380L + V379L + M166F | ++++ | ** | +++ | ** |
| T7C + S47C + H369A + C404V + M166A | +++ | ** | ++++ | ** |
| T7C + S47C + H369A + F22P + M166V | ++++ | ** | +++ | ** |
| T7C + S47C + H369A + L283K + M166S | +++ | ** | ++ | ** |
| T7C + S47C + A33V + A57Y + M166Y | ++++ | ** | +++ | ** |
| T7C + S47C + A33V + A57V + M166G | ++++ | ** | +++ | ** |
| T7C + S47C + Q380L + V379L + M166F + S424A | ++++ | ** | ++++ | ** |
| T7C + S47C + A33V + A57V + M166Y + S424G | +++ | ** | +++ | ** |
| T7C + S47C + Q380L + V379L + F397K + S424L | ++ | ** | +++ | ** |
| T7C + S47C + Q380L + V379L + M166F + R416T | ++++ | ** | ++++ | ** |
| T7C + S47C + S292A + A299P + M166K + R416T | +++ | ** | +++ | ** |
| T7C + S47C + S292A + A299P + M166F + R416P | ++ | ** | +++ | ** |
| T7C + S47C + S292A + A299P + M166F + R416D | ++++ | ** | +++ | ** |
| T7C + S47C + Q380L + V379L + M166F + Y168I | +++++ | ** | +++++ | ** |
| T7C + S47C + Q380L + V379L + M166F + Y168M | +++++ | ** | +++++ | ** |
| T7C + S47C + S292A + A299P + M166E + Y168A | ++++ | ** | +++ | ** |
| T7C + S47C + A334L + F367G + M166S + Y168V | +++ | ** | ++++ | ** |
| T7C + S47C + Q380L + V379L + M166F + N151Q | ++++ | ** | ++++ | ** |
| T7C + S47C + Q380L + V379L + M166F + N151W | ++++ | ** | ++++ | ** |
| T7C + S47C + A334W + F367Q + M166F + N151S | ++++ | ** | +++ | ** |
| T7C + S47C + Q380L + V379L + M166F + N151Y | ++++ | ** | +++ | ** |
| T7C + S47C + Q380L + V379L + M166F + R416D | ++++ | ** | ++++ | ** |
| T7C + S47C + Q380L + V379L + M166F + R416P | ++++ | ** | +++ | ** |
| T7C + S47C + Q380L + V379L + M166F + R416D + I414Q | ++++ | ** | ++++ | ** |
| T7C + S47C + D436A + R457W + M166F + R416D + R444A | ++++ | ** | +++ | ** |
| T7C + S47C + D436A + R444P + M166S + R416F + D436V | +++ | ** | ++++ | ** |
| T7C + S47C + D436A + R444Y + M166S + R416F + G419W | ++++ | ** | ++++ | ** |
| T7C + S47C + Q380L + V379L + M166F + R416D + N151W | +++++ | ** | +++++ | ** |
| T7C + S47C + Q380L + V379L + M166F + R416D + N151F | +++++ | ** | +++++ | ** |
| T7C + S47C + D436A + R457C + M166E + R416Q + N151A | +++++ | ** | +++++ | ** |
| T7C + S47C + D436A + R457P + M166W + R416F + N151V | ++++ | ** | ++++ | ** |
| T7C + S47C + D436A + V379L + M166F + R416D + N151E | ++++ | ** | ++++ | ** |
| T7C + S47C + Q380L + V379L + M166F + R416D + Y168E | ++++ | ** | ++++ | ** |
| T7C + S47C + D396Y + F397Q + M166F + R416D + Y168M | ++++ | ** | ++++ | ** |
| T7C + S47C + D396P + F397S + M166G + R416S + Y168S | ++++ | ** | ++++ | ** |
| T7C + S47C + Q380L + V379L + M166F + R416D + Y168A | ++++ | ** | +++++ | ** |
| T7C + S47C + Q380L + V379L + M166F + R416D + N151W + Y168M | +++++ | ** | ++++ | ** |
| T7C + S47C + D396G + F397Y + M166F + R416D + N151W + Y168A | +++++ | ** | +++++ | ** |
| T7C + S47C + D396G + F397Y + M166D + R416F + N151W + Y168S | ++++ | ** | +++++ | ** |
| T7C + S47C + D396G + F397Y + M166D + R416F + N151W + Y168E | ++++ | ** | +++++ | ** |
| T7C + S47C + Q380L + V379L + M166F + R416D + N151W + S424C | +++++ | ** | +++++ | ** |
| T7C + S47C + Q380L + V379L + M166F + R416D + N151W + S424A | +++++ | ** | +++++ | ** |
| T7C + S47C + Q380L + V379L + M166F + R416D + N151W + S424V | +++++ | ** | ++++ | ** |
| T7C + S47C + Q380L + V379L + M166F + R416D + N151W + F409Q | +++++ | ** | +++++ | ** |
| T7C + S47C + Q380L + V379L + M166F + R416D + N151W + F409V | +++++ | ** | ++++ | ** |
| T7C + S47C + Q380L + V379L + M166F + R416D + N151W + F409H | +++++ | ** | ++++ | ** |
| T7C + S47C + Q380L + V379L + M166F + R416D + N151W + F409M | +++++ | ** | +++++ | ** |
| T7C + S47C + Q380L + V379L + M166F + R416D + N151W + F409T | +++++ | ** | ++++ | ** |
| T7C + S47C + Q380L + V379L + M166F + R416D + N151W + F409A | +++++ | ** | +++++ | ** |
| T7C + S47C + D396G + F397Y + M166A + R416V + N151W + F409M | +++++ | ** | ++++ | ** |
| T7C + S47C + D396G + F397Y + M166A + R416V + N151W + F409T | +++++ | ** | +++++ | ** |
| T7C + S47C + D396G + F397Y + M166A + R416V + N151W + F409A | +++++ | ** | +++++ | ** |
| T7C + S47C + Q380L + V379L + M166F + R416D + N151W + S424V + F409C | ++++ | ** | ++++ | ** |

TABLE 2-continued

| Mutant | Substrate 4 Activity | Substrate 4 ee value | Substrate 5 Activity | Substrate 5 ee value |
|---|---|---|---|---|
| T7C + S47C + Q380L + V379L + M166F + R416D + N151W + S424A + F409Q | +++++ | ** | ++++ | ** |
| T7C + S47C + Q380L + V379L + M166F + R416D + N151W + S424A + F409C | ++++ | ** | ++++ | ** |
| T7C + S47C + Q380L + V379L + M166F + R416D + N151W + F409H + E171T | ++++ | ** | +++++ | ** |
| T7C + S47C + Q380L + V379L + M166F + R416D + N151W + F409H + E171A | +++++ | ** | +++++ | ** |
| T7C + S47C + C404Q + R405F + M166S + R416D + N151W + S424V + F409C | +++++ | ** | +++++ | ** |
| T7C + S47C + C404Q + R405F + M166E + R416M + N151W + S424A + F409Q | ++++ | ** | +++++ | ** |
| T7C + S47C + C404Q + R405F + M166S + R416A + N151W + S424A + F409C | ++++ | ** | +++++ | ** |
| T7C + S47C + C404Q + R405F + M166T + R416A + N151W + F409H + E171T | +++++ | ** | +++++ | ** |
| T7C + S47C + C404Q + R405F + M166Y + R416A + N151W + F409H + E171A | +++++ | ** | +++++ | ** |

The multiple of an activity increase is expressed by +, + means 5-10 times of the increase, ++ means 10-20 times of the increase, +++ means 20-50 times of the increase, ++++ means 50-100 times of the increase, +++++ means more than 100 times of the increase; and * means the ee value is 95%-98%, and ** means the ee value is >98%.

Embodiment 3

Substrate 6

Substrate 7

Substrate 8

10 mg of substrate 6/substrate 7/substrate 8 is respectively dissolved in 30 μL of DMSO to prepare substrate solution. 10 mg of a transaminase, 66.6 μL of isopropylamine hydrochloride solution (6M), 0.1 mg of PLP, and 0.1 M of Tris-Cl buffer (pH 9.0) are successively added to a reaction system so as to make up to a total volume of 500 μL, and finally the prepared substrate solution is added, a pH is adjusted to 9.0, and it is reacted for 16 h at 200 rpm and 45° C. of a constant temperature. 2 times of acetonitrile in volume is added to the reaction system, fully mixed uniformly, standing for 10 min, and centrifuged at 12000 rpm for 10 min, a supernatant is taken, and it is sent to a liquid phase to measure the conversion rate after being diluted by 10 times. ee value detection method: 2 times of the acetonitrile in volume is added to the reaction system, fully mixed uniformly, standing for 10 min, and centrifuged at 12000 rpm for 10 min, a supernatant is taken, anhydrous MgSO$_4$ is added to remove water, it is centrifuged at 12000 rpm for 10 min, a supernatant is taken, N$_2$ is used to blow dry, 1 mL of methanol is added, and it is sent to the liquid phase for detection after being dissolved. The reaction characteristics of some mutants are shown in Table 3:

TABLE 3

| Mutant | Substrate 1 Activity | Substrate 1 ee value | Substrate 2 Activity | Substrate 2 ee value | Substrate 3 Activity | Substrate 3 ee value |
|---|---|---|---|---|---|---|
| Female parent | − | * | − | * | − | * |
| T7C + S47C | ++ | * | ++ | * | + | * |
| Q78C + A330C | ++ | ** | ++ | ** | ++ | ** |
| V137C + G313C | ++ | ** | ++ | ** | ++ | ** |
| A217C + Y252C | ++ | ** | ++ | ** | ++ | ** |
| L295C + C328C | ++ | ** | ++ | ** | ++ | ** |
| T7C + S47C + Q380L + V379L | + | ** | +++ | ** | ++ | ** |
| T7C + S47C + Q380L + V379D | ++ | ** | + | ** | ++ | ** |
| T7C + S47C + Q380L + V379A | ++ | ** | ++ | ** | ++ | ** |
| T7C + S47C + Q380L + V379V | +++ | ** | ++ | ** | ++ | ** |
| T7C + S47C + Q78C + A330C + Y89A | ++ | ** | ++ | ** | + | ** |
| T7C + S47C + Q78C + A330C + Y89E | +++ | ** | ++ | ** | + | ** |
| T7C + S47C + V137C + G313C + Y89V | +++ | * | ++ | ** | +++ | ** |
| T7C + S47C + Q380L + V379L + S156P | +++ | ** | ++ | ** | ++ | ** |
| T7C + S47C + Q78C + A330C + S156Q | ++ | ** | ++ | ** | ++ | ** |
| T7C + S47C + K249F + I400P + S156A | +++ | ** | ++ | ** | + | ** |
| T7C + S47C + Q380L + V379L + M166F | ++ | * | +++ | * | ++ | ** |
| T7C + S47C + H369A + C404V + M166A | ++ | ** | ++++ | ** | +++ | ** |
| T7C + S47C + H369A + F22P + M166V | ++++ | ** | ++ | ** | +++ | ** |

TABLE 3-continued

| Mutant | Substrate 1 Activity | Substrate 1 ee value | Substrate 2 Activity | Substrate 2 ee value | Substrate 3 Activity | Substrate 3 ee value |
|---|---|---|---|---|---|---|
| T7C + S47C + H369A + L283K + M166S | +++ | ** | + | * | +++ | ** |
| T7C + S47C + A33V + A57Y + M166Y | ++ | ** | +++ | ** | ++ | ** |
| T7C + S47C + A33V + A57V + M166G | +++ | ** | +++ | ** | +++ | ** |
| T7C + S47C + Q380L + V379L + M166F + S424A | +++ | ** | +++ | ** | +++ | ** |
| T7C + S47C + A33V + A57V + M166Y + S424G | +++ | * | ++ | ** | +++ | * |
| T7C + S47C + Q380L + V379L + F397K + S424L | ++ | ** | +++ | ** | ++ | ** |
| T7C + S47C + Q380L + V379L + M166F + R416T | ++++ | ** | ++++ | ** | ++ | ** |
| T7C + S47C + S292A + A299P + M166K + R416T | ++ | ** | +++ | * | ++ | ** |
| T7C + S47C + S292A + A299P + M166F + R416P | ++ | ** | +++ | ** | ++ | * |
| T7C + S47C + S292A + A299P + M166F + R416D | +++ | * | +++ | ** | ++++ | ** |
| T7C + S47C + Q380L + V379L + M166F + Y168I | ++++ | ** | +++++ | ** | ++++ | ** |
| T7C + S47C + Q380L + V379L + M166F + Y168M | +++ | ** | +++++ | ** | +++ | ** |
| T7C + S47C + S292A + A299P + M166E + Y168A | +++ | ** | +++ | ** | ++++ | ** |
| T7C + S47C + A334L + F367G + M166S + Y168V | ++ | ** | ++++ | ** | ++++ | ** |
| T7C + S47C + Q380L + V379L + M166F + N151Q | ++++ | * | +++ | ** | ++++ | ** |
| T7C + S47C + Q380L + V379L + M166F + N151W | +++ | ** | +++ | * | ++++ | ** |
| T7C + S47C + A334W + F367Q + M166F + N151S | ++++ | ** | +++ | ** | +++ | ** |
| T7C + S47C + Q380L + V379L + M166F + N151Y | +++ | ** | +++ | ** | +++ | ** |
| T7C + S47C + Q380L + V379L + M166F + R416D | +++ | ** | ++++ | ** | ++ | ** |
| T7C + S47C + Q380L + V379L + M166F + R416P | ++++ | * | +++ | ** | +++ | ** |
| T7C + S47C + Q380L + V379L + M166F + R416D + I414Q | ++++ | ** | ++++ | ** | +++ | ** |
| T7C + S47C + D436A + R457W + M166F + R416D + R444A | +++ | ** | +++ | ** | +++ | ** |
| T7C + S47C + D436A + R444P + M166S + R416F + D436V | +++ | ** | ++++ | ** | +++ | * |
| T7C + S47C + D436A + R444Y + M166S + R416F + G419W | +++ | * | ++++ | ** | +++ | ** |
| T7C + S47C + Q380L + V379L + M166F + R416D + N151W | ++++ | ** | +++++ | ** | ++ | * |
| T7C + S47C + Q380L + V379L + M166F + R416D + N151F | ++++ | ** | +++++ | * | ++++ | ** |
| T7C + S47C + D436A + R457C + M166E + R416Q + N151A | +++++ | ** | +++++ | ** | +++++ | ** |
| T7C + S47C + D436A + R457P + M166W + R416F + N151V | ++++ | ** | ++++ | ** | ++++ | ** |
| T7C + S47C + D436A + V379L + M166F + R416D + N151E | ++++ | * | +++ | ** | +++ | ** |
| T7C + S47C + Q380L + V379L + M166F + R416D + Y168E | +++ | ** | ++++ | ** | ++++ | ** |
| T7C + S47C + D396Y + F397Q + M166F + R416D + Y168M | ++++ | ** | ++++ | ** | ++++ | ** |
| T7C + S47C + D396P + F397S + M166G + R416S + Y168S | +++ | ** | +++ | ** | +++ | ** |
| T7C + S47C + Q380L + V379L + M166F + R416D + Y168A | ++++ | ** | +++ | ** | +++++ | ** |
| T7C + S47C + D396G + F397Y + M166F + R416D + N151W + Y168M | +++++ | ** | +++++ | ** | +++++ | ** |
| T7C + S47C + D396G + F397Y + M166D + R416F + N151W + Y168S | +++ | * | ++++ | ** | +++ | ** |
| T7C + S47C + D396G + F397Y + M166D + R416D + N151W + Y168E | ++++ | ** | ++++ | * | ++++ | * |
| T7C + S47C + Q380L + V379L + M166F + R416D + N151W + S424C | ++++ | ** | ++++ | ** | ++++ | ** |
| | + | | | | + | |
| T7C + S47C + Q380L + V379L + M166F + R416D + N151W + S424A | ++++ | ** | ++++ | ** | +++ | ** |
| T7C + S47C + Q380L + V379L + M166F + R416D + N151W + S424V | ++++ | ** | +++ | ** | +++ | ** |
| T7C + S47C + Q380L + V379L + M166F + R416D + N151W + F409Q | ++++ | ** | ++++ | ** | +++++ | ** |
| T7C + S47C + Q380L + V379L + M166F + R416D + N151 W + F409V | +++++ | ** | ++++ | * | +++++ | ** |
| T7C + S47C + Q380L + V379L + M166F + R416D + N151 W + F409H | ++++ | ** | +++ | ** | +++ | ** |

TABLE 3-continued

| Mutant | Substrate 1 | | Substrate 2 | | Substrate 3 | |
|---|---|---|---|---|---|---|
| | Activity | ee value | Activity | ee value | Activity | ee value |
| T7C + S47C + Q380L + V379L + M166F + R416D + N151W + F409M | +++++ | ** | +++++ | ** | +++ | * |
| T7C + S47C + Q380L + V379L + M166F + R416D + N151W + F409T | ++++ | ** | +++ | ** | ++++ | ** |
| T7C + S47C + Q380L + V379L + M166F + R416D + N151W + F409A | ++++ | ** | ++++ | ** | ++ | ** |
| T7C + S47C + D396G + F397Y + M166A + R416V + N151W + F409M | +++++ | ** | ++++ | ** | +++++ | * |
| T7C + S47C + D396G + F397Y + M166A + R416V + N151W + F409T | ++++ | ** | +++++ | ** | +++++ | ** |
| T7C + S47C + D396G + F397Y + M166A + R416V + N151W + F409A | ++++ | ** | +++++ | ** | +++ | ** |
| T7C + S47C + Q380L + V379L + M166F + R416D + N151W + S424V + F409C | ++++ | ** | ++++ | ** | +++ | ** |
| T7C + S47C + Q380L + V379L + M166F + R416D + N151W + S424A + F409Q | ++++ | ** | +++ | ** | ++++ | ** |
| T7C + S47C + Q380L + V379L + M166F + R416D + N151W + S424A + F409C | ++++ | ** | ++++ | ** | ++++ | ** |
| T7C + S47C + Q380L + V379L + M166F + R416D + N151W + F409H + E171T | +++ | * | +++++ | * | ++++ | * |
| T7C + S47C + Q380L + V379L + M166F + R416D + N151W + F409H + E171A | +++++ | ** | ++++ | ** | ++++ | ** |
| T7C + S47C + C404Q + R405F + M166S + R416D + N151W + S424V + F409C | +++ | ** | +++++ | ** | +++ | ** |
| T7C + S47C + C404Q + R405F + M166E + R416M + N151W + S424A + F409Q | ++++ | ** | ++++ | ** | +++ | ** |
| T7C + S47C + C404Q + R405F + M166S + R416A + N151W + S424A + F409C | ++++ | ** | ++++ | ** | +++ | ** |
| T7C + S47C + C404Q + R405F + M166T + R416A + N151W + F409H + E171T | ++++ | ** | ++++ | ** | ++++ | ** |
| T7C + S47C + C404Q + R405F + M166Y + R416A + N151W + F409H + E171A | +++++ | ** | +++++ | ** | ++++ | ** |

The multiple of an activity increase is expressed by +, + means 5-10 times of the increase, ++ means 10-20 times of the increase, +++ means 20-50 times of the increase, ++++ means 50-100 times of the increase, +++++ means more than 100 times of the increase; and * means the ee value is 95%-98%, and ** means the ee value is >98%.

It may be seen from the above descriptions that the above embodiments of the present disclosure achieve the following technical effects: the transaminase mutant of the present disclosure has the improved enzyme activity, may reduce the amount of the enzyme used in use, and solve the technical problem that the wild-type transaminase is not suitable for the industrial production.

The above are only preferred embodiments of the present disclosure, and are not used to limit the present disclosure. For those skilled in the art, the present disclosure may have various modifications and changes. Any modifications, equivalent replacements, improvement and the like made within the spirit and principle of the present disclosure should be included in a scope of protection of the present disclosure.

The invention claimed is:

1. A transaminase mutant having the amino acid sequence of SEQ ID NO: 1 with the exception of a mutation of more amino acids, wherein the mutation of more amino acids is selected from the group consisting of: T7C+S47C+Q380L+V379L, T7C+S47C+Q380L+V379D, T7C+S47C+Q380L+V379A, T7C+S47C+Q380L+V379V, T7C+S47C+Q78C+A330C+Y89A, T7C+S47C+Q78C+A330C+Y89E, T7C+

S47C+V137C+G313C+Y89V, T7C+S47C+Q380L+V379L+S156P, T7C+S47C+Q78C+A330C+S156Q, T7C+S47C+K249F+1400P+S156A, T7C+S47C+Q380L+V379L+M166F, T7C+S47C+H369A+C404V+M166A, T7C+S47C+H369A+F22P+M166V, T7C+S47C+H369A+L283K+M166S, T7C+S47C+A33V+A57Y+M166Y, T7C+S47C+A33V+A57V+M166G, T7C+S47C+Q380L+V379L+M166F+S424A, T7C+S47C+A33V+A57V+M166Y+S424G, T7C+S47C+Q380L+V379L+F397K+S424L, T7C+S47C+Q380L+V379L+M166F+R416T, T7C+S47C+S292A+A299P+M166K+R416T, T7C+S47C+S292A+A299P+M166F+R416P, T7C+S47C+S292A+A299P+M166F+R416D, T7C+S47C+Q380L+V379L+M166F+Y168I, T7C+S47C+Q380L+V379L+M166F+Y168M, T7C+S47C+S292A+A299P+M166E+Y168A, T7C+S47C+A334L+F367G+M166S+Y168V, T7C+S47C+Q380L+V379L+M166F+N151Q, T7C+S47C+Q380L+V379L+M166F+N151W, T7C+S47C+A334W+F367Q+M166F+N151S, T7C+S47C+Q380L+V379L+M166F+N151Y, T7C+S47C+Q380L+V379L+M166F+R416D, T7C+S47C+Q380L+V379L+M166F+R416P, T7C+S47C+Q380L+V379L+M166F+R416D+1414Q, T7C+S47C+D436A+R457W+M166F+R416D+R444A, T7C+S47C+D436A+R444P+M166S+R416F+D436V, T7C+S47C+D436A+R444Y+M166S+R416F+G419W, T7C+S47C+Q380L+V379L+M166F+R416D+N151W, T7C+S47C+Q380L+V379L+M166F+R416D+N151F, T7C+S47C+D436A+R457C+M166E+R416Q+N151A, T7C+S47C+D436A+R457P+M166W+R416F+N151V, T7C+S47C+D436A+V379L+M166F+R416D+N151E, T7C+S47C+Q380L+V379L+M166F+R416D+Y168E, T7C+S47C+D396Y+F397Q+M166F+R416D+Y168M, T7C+S47C+D396P+F397S+M166G+R416S+Y168S, T7C+S47C+Q380L+V379L+M166F+R416D+Y168A, T7C+S47C+Q380L+V379L+M166F+R416D+N151W+Y168M, T7C+S47C+D396G+F397Y+M166F+R416D+N151W+Y168A, T7C+S47C+D396G+F397Y+M166D+R416F+N151W+Y168S, T7C+S47C+D396G+F397Y+M166D+R416D+N151W+Y168E, T7C+S47C+Q380L+V379L+M166F+R416D+N151W+S424C, T7C+S47C+Q380L+V379L+M166F+R416D+N151W+S424A, T7C+S47C+Q380L+V379L+M166F+R416D+N151W+S424V, T7C+S47C+Q380L+V379L+M166F+R416D+N151W+F409Q, T7C+S47C+Q380L+V379L+M166F+R416D+N151W+F409V, T7C+S47C+Q380L+V379L+M166F+R416D+N151W+F409H, T7C+S47C+Q380L+V379L+M166F+R416D+N151W+F409M, T7C+S47C+Q380L+V379L+M166F+R416D+N151W+F409T, T7C+S47C+Q380L+V379L+M166F+R416D+N151W+F409A, T7C+S47C+D396G+F397Y+M166A+R416V+N151W+F409M, T7C+S47C+D396G+F397Y+M166A+R416V+N151W+F409T, T7C+S47C+D396G+F397Y+M166A+R416V+N151W+F409A, T7C+S47C+Q380L+V379L+M166F+R416D+N151W+S424V+F409C, T7C+S47C+Q380L+V379L+M166F+R416D+N151W+S424A+F409Q, T7C+S47C+Q380L+V379L+M166F+R416D+N151W+S424A+F409C, T7C+S47C+Q380L+V379L+M166F+R416D+N151W+F409H+E171T, T7C+S47C+Q380L+V379L+M166F+R416D+N151W+F409H+E171A, T7C+S47C+C404Q+R405F+M166S+R416D+N151W+S424V+F409C, T7C+S47C+C404Q+R405F+M166E+R416M+N151W+S424A+F409Q, T7C+S47C+C404Q+R405F+M166S+R416A+N151W+S424A+F409C, T7C+S47C+C404Q+R405F+M166T+R416A+N151W+F409H+E171T, or T7C+S47C+C404Q+R405F+M166Y+R416A+N151W+F409H+E171A; and the transaminase mutant has improved stereoselectivity and enhanced activity compared to the wild type transaminase having the amino acid sequence of SEQ ID NO:1.

2. A DNA molecule, wherein the DNA molecule encodes the transaminase mutant according to claim 1.

3. A recombinant plasmid, wherein the recombinant plasmid contains the DNA molecule according to claim 2.

4. The recombinant plasmid according to claim 3, wherein the recombinant plasmid is pET-22a(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

5. A host cell, wherein the host cell contains the recombinant plasmid according to claim 3.

6. The host cell according to claim 5, wherein the host cell comprises a prokaryotic cell or a eukaryotic cell.

7. A method for producing a chiral amine, comprising a step of catalyzing a transamination reaction of a ketone compound and an amino donor by a transaminase, wherein the transaminase is the transaminase mutant according to claim 1.

8. The method according to claim 7, wherein the ketone compound is 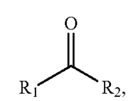 and a product of the transamination reaction is 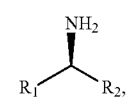 wherein, $R_1$ and $R_2$ each independently represent an optionally substituted or unsubstituted alkyl, an optionally substituted or unsubstituted aralkyl, or an optionally substituted or unsubstituted aryl; the $R_1$ and $R_2$ can be singly or combined with each other to form a substituted or unsubstituted ring.

9. The method according to claim 7, wherein the amino donor is isopropylamine or alanine.

10. The method according to claim 7, wherein in a reaction system in which the transaminase catalyzes the transamination reaction of the ketone compound and the amino donor, a pH is 7~11.

11. The host cell according to claim 6, wherein the prokaryotic cell is an *E. coli* BL21-DE3 cell or an *E. coli* Rosetta-DE3 cell; the eukaryotic cell is yeast.

12. The method according to claim 8, wherein the ketone compound is a dihydroxy ketal compound, and the reaction is a transamination reaction for generating

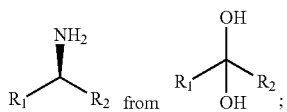

from the $R_1$ and $R_2$ are an optionally substituted or unsubstituted alkyl having 1~20 carbon atoms, an optionally substituted or unsubstituted aralkyl, or an optionally substituted or unsubstituted aryl.

13. The method according to claim 12, wherein the substitution refers to substitution by a halogen atom, a nitrogen atom, a sulfur atom, a hydroxyl, a nitro group, a cyano group, a methoxy, an ethoxy, a carboxyl, a carboxymethyl, a carboxyethyl or a methylenedioxy.

14. The method according to claim 12, wherein the $R_1$ represents a methyl or a halogen-substituted methyl.

15. The method according to claim 12, wherein the ketone compound

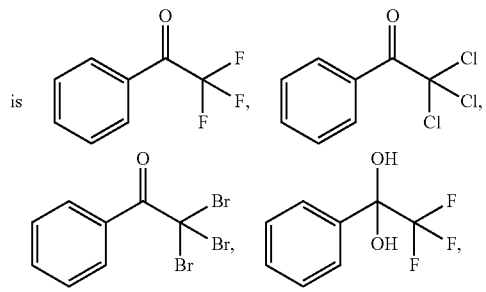

is

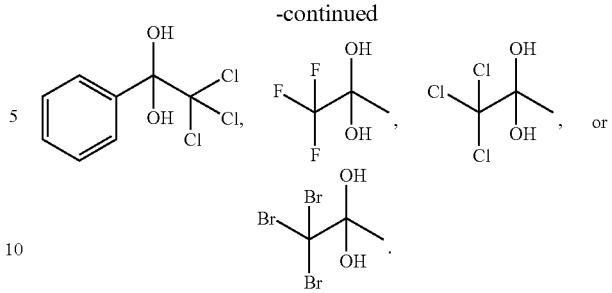

16. The method according to claim 10, wherein the volume concentration of dimethyl sulfoxide in the reaction system for catalyzing the transamination reaction of the ketone compound and the amino donor by the transaminase is 0%~50%.

17. The method according to claim 10, wherein the temperature of the reaction system for catalyzing the transamination reaction of the ketone compound and the amino donor by the transaminase is 25° C.-60° C.

18. The method according to claim 12, wherein the optionally substituted or unsubstituted alkyl having 1-10 carbon atoms, an optionally substituted or unsubstituted aralkyl, or an optionally substituted or unsubstituted aryl.

19. The method according to claim 14, wherein the halogen-substituted methyl is $CF_3$, $CF_2H$, $CCl_3$, $CCl_2H$, $CBr_3$ or $CBr_2H$.

20. The method according to claim 16, wherein the volume concentration of dimethyl sulfoxide in the reaction system for catalyzing the transamination reaction of the ketone compound and the amino donor by the transaminase is 0%-20%.

* * * * *

SEQUENCE LISTING

<160> NUMBER OF SEQ ID NOS: 1

<210> SEQ ID NO 1
<211> LENGTH: 459
<212> TYPE: PRT
<213> ORGANISM: Chromobacterium violaceum

<400> SEQUENCE: 1

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu

```
              65                  70                  75                  80
Glu Leu Pro Phe Tyr Asn Thr Phe Tyr Lys Thr Thr His Pro Ala Val
                    85                  90                  95
Val Glu Leu Ser Ser Leu Leu Ala Glu Val Thr Pro Ala Gly Phe Asp
                    100                 105                 110
Arg Val Phe Tyr Thr Asn Ser Gly Ser Glu Ser Val Asp Thr Met Ile
                    115                 120                 125
Arg Met Val Arg Arg Tyr Trp Asp Val Gln Gly Lys Pro Glu Lys Lys
        130                 135                 140
Thr Leu Ile Gly Arg Trp Asn Gly Tyr His Gly Ser Thr Ile Gly Gly
145                 150                 155                 160
Ala Ser Leu Gly Gly Met Lys Tyr Met His Glu Gln Gly Asp Leu Pro
                    165                 170                 175
Ile Pro Gly Met Ala His Ile Glu Gln Pro Trp Trp Tyr Lys His Gly
                180                 185                 190
Lys Asp Met Thr Pro Asp Glu Phe Gly Val Val Ala Ala Arg Trp Leu
            195                 200                 205
Glu Glu Lys Ile Leu Glu Ile Gly Ala Asp Lys Val Ala Ala Phe Val
    210                 215                 220
Gly Glu Pro Ile Gln Gly Ala Gly Gly Val Ile Val Pro Pro Ala Thr
225                 230                 235                 240
Tyr Trp Pro Glu Ile Glu Arg Ile Cys Arg Lys Tyr Asp Val Leu Leu
                245                 250                 255
Val Ala Asp Glu Val Ile Cys Gly Phe Gly Arg Thr Gly Glu Trp Phe
                260                 265                 270
Gly His Gln His Phe Gly Phe Gln Pro Asp Leu Phe Thr Ala Ala Lys
        275                 280                 285
Gly Leu Ser Ser Gly Tyr Leu Pro Ile Gly Ala Val Phe Val Gly Lys
    290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                325                 330                 335
Ala Ala Leu Arg Asp Glu Gly Ile Val Gln Arg Val Lys Asp Asp Ile
                340                 345                 350
Gly Pro Tyr Met Gln Lys Arg Trp Arg Glu Thr Phe Ser Arg Phe Glu
            355                 360                 365
His Val Asp Asp Val Arg Gly Val Met Val Gln Ala Phe Thr Leu
    370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Arg
                405                 410                 415
Ser Cys Gly Asp His Ile Val Ser Ala Pro Pro Leu Val Met Thr Arg
                420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
    450                 455
```